United States Patent [19]

Garsky

[11] 4,000,259

[45] Dec. 28, 1976

[54] CYCLIC DODECAPEPTIDE ANALOGS OF SOMATOSTATIN AND INTERMEDIATES

[75] Inventor: Victor M. Garsky, Havertown, Pa.

[73] Assignee: American Home Products Corporation, New York, N.Y.

[22] Filed: June 16, 1975

[21] Appl. No.: 587,014

[52] U.S. Cl. .............................. 424/177; 260/78 A; 260/112.5 S
[51] Int. Cl.² ................ A61K 37/00; C07C 103/52
[58] Field of Search ............................ 260/112.5 S

[56] References Cited

UNITED STATES PATENTS 3,917,581  11/1975  Immer et al. ............... 260/112.5 S

*Primary Examiner*—Lewis Gotts
*Assistant Examiner*—Reginald J. Suyat

[57] ABSTRACT

Cyclic dodecapeptide analogs of somatostatin without cysteine amino acid residues and intermediates obtained in the synthesis of such compounds are described. These cyclic dodecapeptides inhibit the secretion of glucagon and hence have application in the treatment of diabetes mellitus.

13 Claims, No Drawings

CYCLIC DODECAPEPTIDE ANALOGS OF SOMATOSTATIN AND INTERMEDIATES

This invention relates to cyclic dodecapeptide analogs of somatostatin and intermediates obtained in their synthesis by a combination of the solid phase and classical method of peptide synthesis.

Somatostatin (also known as somatotropin release inhibiting factor or SRIF) is the

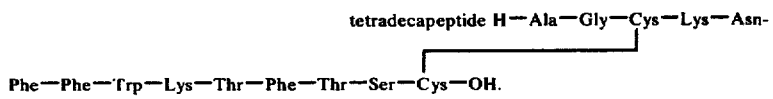

This tetradecapeptide has been identified by isolation from extracts of ovine hypothalamic tissues and found to inhibit the secretion of the hormone somatotropin which is commonly referred to as the growth hormone (GH); See Brazeau et al., Science, 179 pp 77–79 (Jan. 1973). The linear form of this tetradecapeptide, H-Ala-Gly-Cys-Lys-Asn-Phe-Phe-Trp-Lys-Thr-Phe-Thr-SER-Cys-OH, has also been reported by Brazeau et al., supra, to have been synthesized by solid phase methodology and found to have the same biological activity as the somatostatin obtained from a natural source. In copending application Ser. No. 430,441 filed Jan. 3, 1974, now U.S. Pat. No. 3,882,098, the undecapeptide Des-Ala[1]-Gly[2]-Asn[5]-SRIF and its oxidized form are described and in copending application Ser. No. 457,038 filed Apr. 1, 1974, the dodecapeptide Des-Ala[1]-Gly[2]-SRIF and its oxidized form are described.

Cyclic analogs of somatostatin not containing cysteine have not been reported in the prior art. Thus, the cyclic dodecapeptides of the present invention possess a cyclic structure which contains no sulfur but carbon as a ring member, eliminates the amino acids from the one and two positions of somatostatin (i.e. Ala and Gly) and replaces them with the lysyl amino acid residue or homologs thereof and replaces Cys[14] with aspartic acid or homologs thereof.

The cyclic dodecapeptides of the present invention which inhibit the release of glucagon are represented by the formula

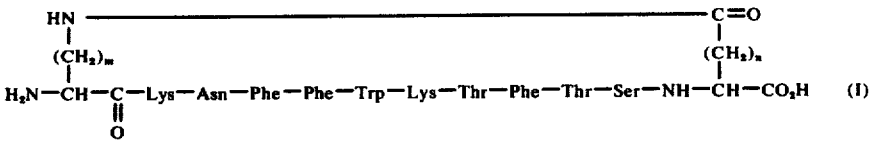

and the non-toxic acid addition salts thereof; and wherein m and n are whole numbers from 1 through 5; where $m=1$ the N-terminal amino acid residue is $\alpha,\beta$-diaminopropionic acid; where $m=2$ the N-terminal amino acid residue is $\alpha,\gamma$-diaminobutyric acid; where $m=3$ the N-terminal amino acid residue is ornithine; and where $m=4$ the N-terminal amino acid residue is lysine; and where $m=5$ the N-terminal amino acid is $\alpha,\gamma$-diaminoheptanoic acid; where $n=1$ the C-terminal amino acid is aspartic acid; where $n=2$ the C-terminal amino acid is glutamic acid; where $n=3$ the C-terminal amino acid is $\alpha$-aminoadipic acid; where $n=4$ the C-terminal amino acid is $\alpha$-aminopimelic acid; and where $n=5$ the C-terminal amino acid is $\alpha$-aminosuberic acid. The preferred compound of formula I is one in which $m=4$ and $n=1$.

Illustrative of acid addition salts are hydrochloride, hydrobromide, sulfate, phosphate, maleate, acetate, citrate, benzoate, succinate, malate, ascorbate and the like.

The nomenclature used to depict the peptides follows that adopted by Schroder & Lubke, "The Peptides," I, pp. viii-xxix (Academic Press 1965). All chiral amino acid residues identified in formula I and the other formulas hereinafter are of the natural or L-configuration unless specified otherwise.

The present invention also relates to novel undecapeptide intermediates of the formula:

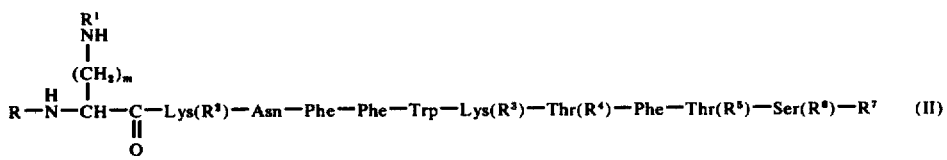

wherein:

R is an $\alpha$-amino protecting group. The $\alpha$-amino protecting groups contemplated by R are those known to be useful in the art in the step-wise synthesis of polypeptides. Among the classes of $\alpha$-amino protecting groups covered by R are (1) acyl type protecting groups illustrated by the following: formyl, trifluoroacetyl, phthalyl, toluenesulfonyl (tosyl), benzensulfonyl, nitrophenylsulfenyl, tritylsulfenyl, o-nitrophenoxyacetyl, $\gamma$-chlorobutyryl, etc; (2) aromatic urethan type protecting groups illustrated by benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl, 1-(p-biphenyly)-1-methylethoxycarbonyl, $\alpha,\alpha$-dimethyl-3,5-dimethoxybenzyloxycarbonyl and benzhydryloxycarbonyl; (3) aliphatic urethan protecting groups illustrated by tert-butyloxycarbonyl, diisopropylmethoxycarbonyl, isopropyloxycarbonyl, ethoxycarbonyl, allyloxycarbonyl; (4) cycloalkyl urethan type protecting groups illustrated by cyclopentyloxycarbonyl, adamantyloxycarbonyl, cyclohexyloxycarbonyl; (5) thio urethan type protecting groups such as phenylthiocarbonyl; (6) alkyl type protecting groups as illustrated by triphenylmethyl (trityl), benzyl; (7) trialkylsilane groups such as trimethylsilane. The preferred α-amino protecting group defined by R is tert-butyloxycarbonyl;

$R^1$ is an acid labile or photolytic labile protecting group for the side chain amino substituent of the amino residue in the one position of the undecapeptide of formula II (e.g. lysyl, ornithyl, etc.). The selection of this side chain amino protecting group is critical in that it must be one which can be removed by cleavage under conditions that will not cleave off the side chain amino protecting groups $R^2$ and $R^3$ on the lysyl residues in positions two and seven of the undecapeptide nor cleave the α-amino protecting group defined by R. Hence, $R^1$ cannot be the same as R, $R^2$ or $R^3$. Illustrative of suitable protecting groups defined by $R^1$ are biphenylisopropyloxycarbonyl, t-butyloxycarbonyl, trityl, t-amyloxycarbonyl, isopropyloxycarbonyl, α,α-dimethyl 3,5-dimethoxybenzyloxycarbonyl, sec butyloxycarbonyl, 3,5-dimethoxybenzyloxycarbonyl, etc. Preferably $R^1$ is t-butyloxycarbonyl.

$R^2$ and $R^3$ is a protecting group for the side chain amino substituent of lysine in the two and seven position of the undecapeptide of formula II. Illustrative of suitable side chain amino protecting groups are benzyloxycarbonyl and substituted benzyloxycarbonyl said substituent being selected from halo (e.g. chloro, bromo, fluoro) and nitro (e.g. 2-chlorobenzyloxycarbonyl, p-nitrobenzyloxycarbonyl, 3,4-dichlorobenzyloxycarbonyl), tosyl, t-amyloxycarbonyl, t-butyloxycarbonyl, diisopropylmethoxycarbonyl; etc. The selection of such a side chain amino protecting group is critical in that it must be one which is not removed by cleavage during cleavage of the $R^1$ protecting group from the amino acid residue in the one position. Hence, the $R^1$ side chain amino protecting group cannot be the same as the $R^2$ and $R^3$ protecting groups. If $R^2$ and $R^3$ were t-butyloxycarbonyl $R^1$ would have to be a protecting group that is more acid sensitive and hence cleavable under conditions that will not cleave t-butyloxycarbonyl. Thus, $R^1$ can be biphenylisopropyloxycarbonyl.

$R^4$, $R^5$ and $R^6$ are protecting groups for the alcoholic hydroxyl group of threonine and serine and is selected from the class consisting of acetyl, benzoyl, tert-butyl, trityl, benzyl, 2,6-dichlorobenzyl benzyloxycarbonyl. The preferred protecting group is benzyl; or $R^4$ and/or $R^5$ and/or $R^6$ is hydrogen which means there is no protecting group on the alcoholic hydroxyl function;

$R^7$ is selected from the class consisting of OH, $NHNH_2$, $N_3$, $OCH_3$ and

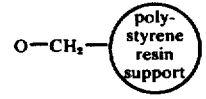

The polystyrene resin support is preferably a copolymer of styrene with about 1 to 2% divinyl benzene as a cross linking agent which causes the polystyrene polymer to be completely insoluble in certain organic solvents. The polystyrene polymer is composed of long alkyl chains bearing a phenyl ring on every second carbon and the terminal amino acid residue (Ser) is joined through a covalent carbon to carbon bond to these phenyl rings. The alkyl chains are cross linked at approximately every fiftieth carbon by p-diethylphenyl residues derived from divinyl benzene.

A further aspect of the present invention relates to novel dodecapeptides of the formula:

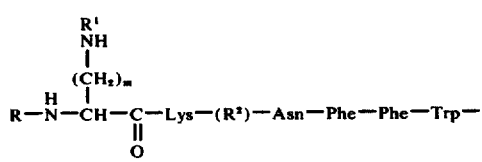 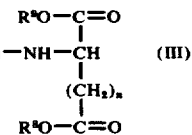 (III)

and

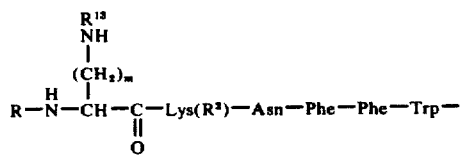 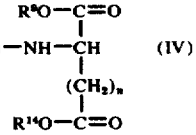 (IV)

wherein:

R, $R^2$, $R^3$, $R^4$, $R^5$ and $R^6$ have the same meaning as set forth in connection with formula II;

$R^8$ is a side chain carboxyl protecting group which is removed under conditions which will not remove the $R^9$ α-carboxyl protecting group. Thus $R^8$ and $R^9$ cannot be the same protecting group. Illustrative of $R^8$ side chain carboxyl protecting groups are t-butyl and benzhydryl;

$R^9$ is a α-carboxyl protecting group. The α-carboxyl protecting group represented by $R^9$ is one which is stable under conditions which (1) remove the $R^8$ carboxyl protecting group, if one is present and (2) remove the $R^1$ side chain α-amino protecting group on the amino acid residue in the one position of the dodecapeptide. The $R^9$ carboxyl protecting group is illustrated by $C_1$–$C_6$ alkyl (e.g. methyl, ethyl, butyl, pentyl, isobutyl), benzyl, substituted benzyl (wherein the substituent is selected from at least one of nitro, methoxy and methyl e.g. p-methoxybenzyl, 2,4-dimethoxybenzyl, p-nitrobenzyl, 2,4,6-trimethylbenzyl), phenacyl, phthalimidomethyl, benzhydryl, trichloroethyl, 4-picolyl, β-methylthioethyl and 4-(methylthio) phenyl. The preferred $R^9$ group is benzyl.

$R^{13}$ is selected from the class consisting of hydrogen and $R^1$;

$R^{14}$ is selected from the class consisting of hydrogen and $R^8$; and at least one of $R^{13}$ and $R^{14}$ being hydrogen.

The present invention also contemplates intermediates of the formula:

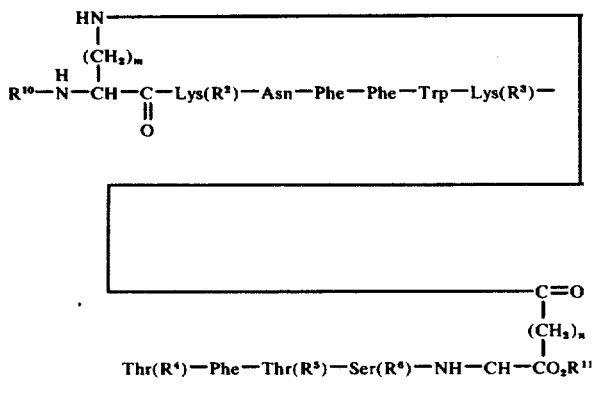

wherein:

$R^2$, $R^3$, $R^4$, $R^5$ and $R^6$ have the same meaning as in formula II;

$R^{10}$ is a member selected from the class consisting of hydrogen and R; and $R^{11}$ is a member selected from the class consisting of hydrogen and $R^9$;

The novel decapeptides of formula II are prepared using solid phase synthesis. The synthesis is commenced from the C-terminal end of the peptide using an α-amino protected resin. Such a starting material can be prepared by attaching an α-amino protected serine to a chloromethylated resin or a hydroxymethyl resin. The preparation of the hydroxymethyl resin is described by Bodanszky et al., Chem. Ind. (London) 33, 1597–98 (1966). A chloromethylated resin is commercially available from Bio Rad Laboratories Richmond, California and the preparation of such a resin is described by Stewart et al., "Solid Phase Peptide Synthesis" (Freeman & Co., San Francisco 1969), Chapter 1, pp 1–6. The α-amino and side chain protected serine is coupled to the chloromethylated resin according to the procedure of Gisin, Helv. 56 p 1476 (1973). Following the coupling of the α-amino and side chain protected serine to the resin support, the α-amino protecting group is removed such as by using trifluoroacetic acid in methylene chloride, trifluoroacetic acid alone or HCl in dioxane. The deprotection is carried out at a temperature between about 0° C and room temperature. Other standard cleaving reagents and conditions for removal of specific α-amino protecting groups may be used as described in Schroder & Lubke, supra, 1 pp. 72–75. After removal of the α-amino protecting group the remaining α-amino protected amino acids are coupled step-wise in the desired order to obtain a compound of formula (II) or as an alternate to adding each amino acid separately to the synthesis, some of them may be coupled prior to addition to the solid phase reactor. The selection of an appropriate coupling reagent is within the skill of the art. A particularly suitable coupling reagent is N,N'-diisopropylcarbodiimide. As previously indicated, the activating reagents used in the aforedescribed synthesis are those well known in the peptide art. Illustrative of these are (1) carbodiimides (e.g. N,N'-dicyclohexylcarbodiimide, N-ethyl N'-(γ-dimethylamino propyl carbodiimide); (2) cyanamides (e.g. N,N-dibenzylcyanamide; (3) ketenimines; (4) isoxazolium salts (e.g. N-ethyl-5-phenyl isoxazolium-3¹-sulfonate; (5) monocyclic nitrogen containing heterocyclic amides of aromatic character containing one through four nitrogens in the ring such as imidazolides, pyrazolides, 1,2,4-triazolides. Specific heterocyclic amides that are useful include N,N'-carbonyldiimidazole, N,N¹-carbonyl-di-1,2,4-triazole; (6) alkoxylated acetylene (e.g. ethoxyacetylene); (7) reagents which form a mixed anhydride with the carboxyl moiety of the amino acid (e.g. ethylchloroformate, isobutylchloroformate) and (8) nitrogen-containing heterocyclic compounds having a hydroxy group on one ring nitrogen (e.g. N-hydroxyphthalimide, N-hydroxysuccinimide, 1-hydroxybenzotriazole). Other activating reagents and their use in peptide coupling are described by Schroder & Lubke supra, in Chapter III and by Kapoor, J. Pharm. Sci., 59, pp 1–27, (1970).

Each protected amino acid or amino acid sequence is introduced into the solid phase reactor in about a four-fold excess and the coupling is carried out in a medium of dimethylformamide: methylene chloride (1:1) or in dimethylformamide or methylene chloride alone. In cases where incomplete coupling occurred the coupling procedure is repeated before removal of the αa-amino protecting group, prior to the coupling of the next amino acid to the solid phase reactor. The success of the coupling reaction at each stage of the synthesis is monitored by the ninhydrin reaction as described by E. Kaiser et al., Analyt. Biochem, 34, 595 (1970).

After the desired amino acid sequence of formula II has been obtained the peptide is removed from the resin. This can be done by methanolysis to obtain a compound of the formula

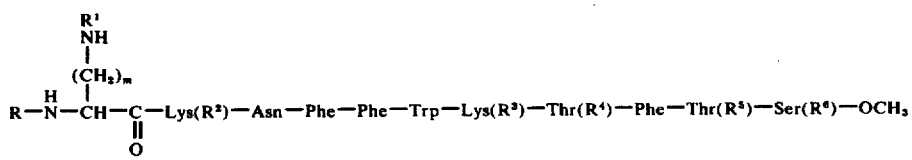

This C-terminal methyl ester is converted to the corresponding acid by hydrolysis followed by activation of the carboxyl group and formation of the hydrazide by classical methods of peptide synthesis to obtain a compound of formula III. However, the preferred procedure for obtaining a compound of formula I is in accordance with the reaction scheme shown in the flow diagram appended hereto. With reference to the flow diagram, a undecapeptide is linked to a resin to obtain a compound of the formula

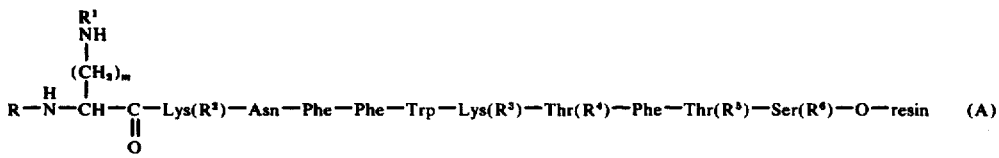

is converted to the corresponding hydrazide of the formula

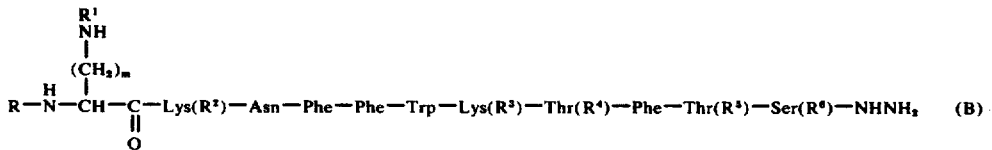

by reaction with hydrazine. The hydrazide of formula B is then converted to the corresponding azide of the formula

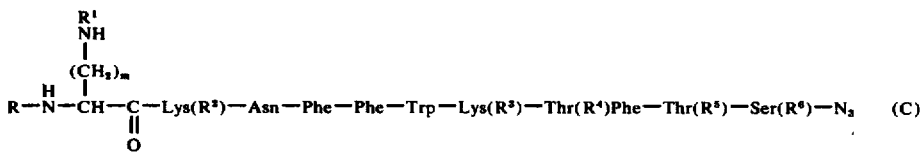

by reaction with a reagent which furnishes nitrous acid in situ. Suitable reagents for this purpose include a lower alkyl nitrite (e.g. t-butyl nitrite, isoamyl nitrite) or an alkali metal nitrite salt (e.g. sodium nitrite, potassium nitrite) in the presence of a strong acid such as hydrochloric, phosphoric, sulfonic, etc. This reaction is carried out in the presence of either water and/or a non-aqueous solvent such as dimethylformamide, tetrahydrofuran, dioxane, chloroform, methylene chloride, etc., at a temperature between about −40° C and +20° C. The azide of formula C which is preferably not isolated from the reaction medium is then coupled with an amino acid of the formula

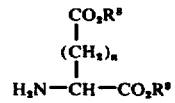

wherein n is a whole number from 1 through 5; to obtain a dodecapeptide of the formula:

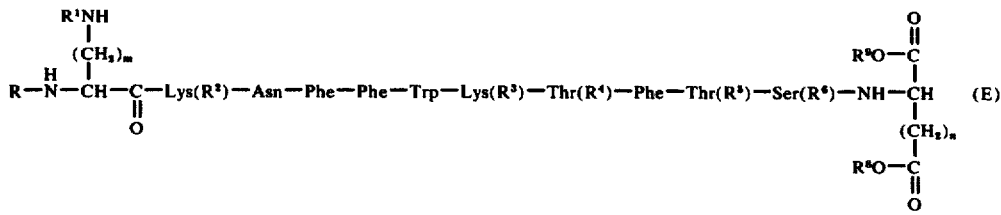

This coupling is carried out between a temperature of about −50° C and +50° C, preferably between about −25°C and +10° C.

The dodecapeptide of formula (E) is then reacted with a cleaving reagent that will split off both the side chain amino protecting group $R^1$ on the amino acid residue in the one position of the dodecapeptide as well as the $R^8$ carboxyl protecting group, if one is present, to yield a compound of the formula

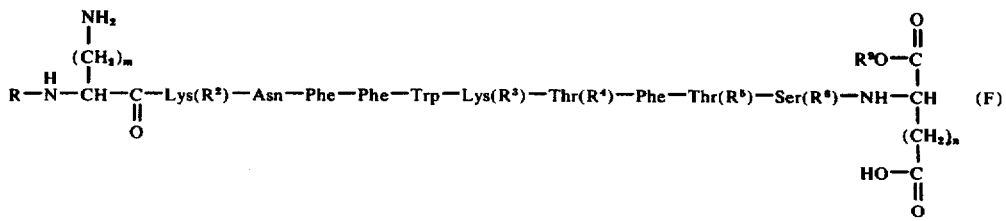

which corresponds to a compound of formula IV wherein each of $R^{13}$ and $R^{14}$ is hydrogen. This cleavage can also be done selectively, if desired, to first remove the $R^1$ protecting group followed by cleavage of the $R^8$ protecting group or vis a versa to obtain a compound of formula (IV) wherein one of $R^{13}$ and $R^{14}$ is other than hydrogen. It is essential that the cleaving reagent be one which does not split off at this stage of the synthesis the (1) $R^2$ and $R^3$ side chain amino protecting group on the lysyl amino acid residue in positions two and seven of the dodecapeptide, (2) α-amino protecting group R, (3) α-carboxyl protecting group $R^9$. A particularly suitable cleaving reagent is trifluoroacetic acid where R is benzyloxycarbonyl, $R^1$ is t-butyloxycarbonyl, $R^2$ and $R^3$ are 2-chlorobenzyloxycarbonyl, $R^8$ is t-butyl and $R^9$ is benzyl. The selection of other compatible reagents for removal of the $R^1$ side chain amino protecting group without cleavage of the R, $R^2$ and $R^3$ protecting groups is described by Schroder & Lubke, supra, 1 pp 72–75, the disclosure of which is incorporated herein by reference. While it is preferred that the side chain protecting groups represented by $R^4$, $R^5$ and $R^6$ not be split off during the formation of a compound of formula F, such groups can be cleaved, if desired so as to obtain a compound of the formula J. Pharm. Science, 61 pp. 1345–1356 (1972) the disclosure of which is incorporated herein by reference.

A compound of formula G is then converted to a compound of formula I by cleaving the $R^2$ and $R^3$ side chain amino protecting groups, the R α-amino protecting group, the $R^9$ α-carboxyl protecting group along with any protecting groups represented by $R^4$, $R^5$ and $R^6$. Suitable cleaving systems are hydrogen over a palladium catalyst or hydrogen fluoride. The cleavage step, if desired, can be carried out step wise by the selection of a reagent that will only cleave the $R^9$ α-carboxyl protecting group, followed by use of a reagent that will cleave the R α-amino protecting group and any other side chain protecting groups. Alternatively the R α-amino protecting group can be cleaved first followed by simultaneous or sequential cleavage of the other protecting groups including the $R^9$ α-carboxyl group. The selection of suitable cleaving reagents that are compatible with the particular -60 -amino, side chain and α-carboxyl protecting groups that can be used are described by Schroeder and Lubke, supra, pp 72–75.

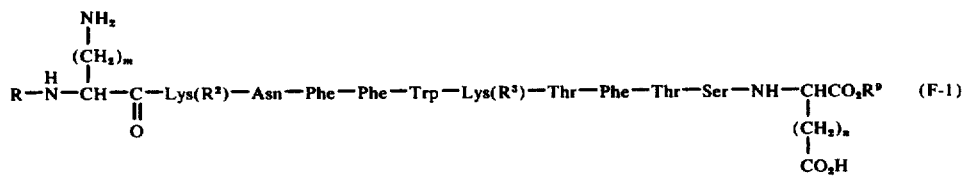

The compound of formula F is then cyclized to produce a compound of the formula

An alternate route to preparing the compounds of formula (V) is to convert a compound of the formula

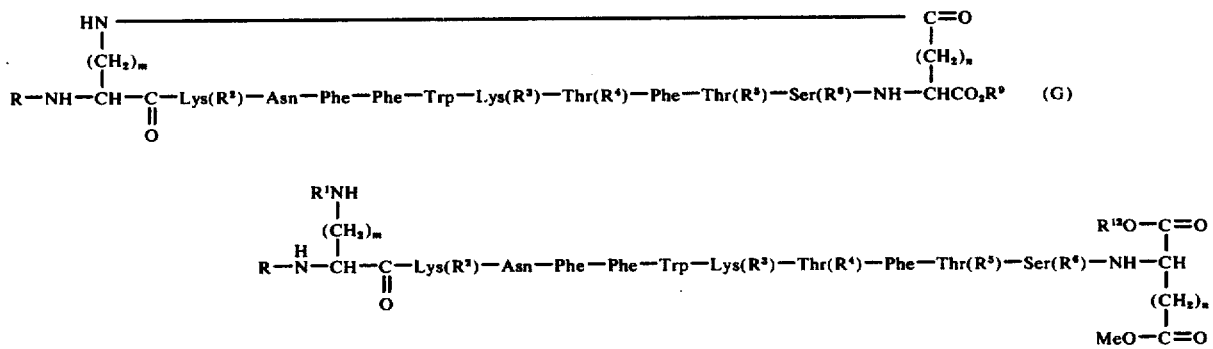

This cyclization is preferably carried out using N,N'-dicyclohexylcarbondiimide (DCC) and N-hydroxybenzotriazole in the presence of an organic solvent in a temperature range between −40° C and +20° C. Suitable solvents include dimethylformamide, dichloromethane, chloroform, dioxane, tetrahydrofuran and mixtures thereof. Other cyclization reagents may also be used as exemplified by the coupling reagents described supra in connection with the preparation of the decapeptide-resin as well as those described by Kopple, wherein $R^{12}$ is selected from the class consisting of hydrogen and $R^9$ and Me is methyl, to the corresponding hydrazide by reaction with hydrazine to obtain

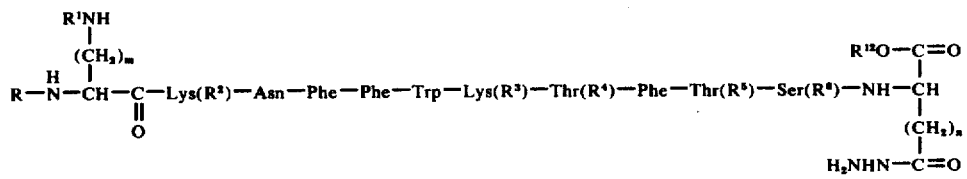

and thereafter converting this compound to the corresponding azide by reaction with a reagent that will yield nitrous acid in situ as previously described. The azide is then cyclized after first removing the $R^1$ side chain amino protecting group.

The materials represented by formula D are known prior art materials and/or can be readily prepared by conventional techniques from the well known unprotected amino acids, namely aspartic acid, glutamic acid, α-aminoadipic acid, α-aminopimelic acid and -60-aminosuberic acid. The preparation of these amino acids is described by Farkasova et at., Col. Czechoslov. Chem. Commun. 30, 3117 (1965); The preparation of ω-carboxyl protected esters is described by Schroder et al., Annalen 673, pp 196, 208 (1964) and Rudinger et al., Col. Czechoslov. Chem. Commun. 32, 1229 (1967).

The amino acids used in the one position of the cyclic dodecapeptides of the present invention are either commercially available and/or described in the prior art. Thus, lysine and ornithine as well as protected derivatives thereof are commercially available from Bachem, Inc., Marina Del Ray, Calif. The amino acid α,β-diaminopropionic acid is available from Calbiochem, San Diego, Calif. and α,γ-diaminobutyric acid is available from Aldrich Chem. Milwaukee, Wis. For a literature reference see Ahlfeld et al., - Bull Res. Coun. Israel, Sec. A, 84, pp 115 (1959).

The following examples are illustrative of the preparation of the compounds of formulas of the present invention.

EXAMPLE 1

Benzyloxycarbonyl-N$^\epsilon$ -(t-butyloxycarbonyl)-L-lysyl-N$^\epsilon$ -(2-chlorobenzyloxycarbonyl)-L-lysyl-asparaginyl-L-phenylalanyl-L-phenylalanyl-L-trytophyl-N$^\epsilon$ -(2-chlorobenzyloxycarbonyl)-L-lysyl-O-benzyl-L-threonyl-L-phenylalanyl-O-benzyl-L-threonyl-O-benzyl-L-serine methylated polystyrene resin Chloromethylated polystyrene resin (20.0 g, 0.75 m moles Cl/g) is heated in a 500 ml round bottom flask with t-butyloxycarbonyl-O-benzyl-L-serine (9.2 g, 31 m moles) and potassium tertiarybutyl alcoholate (3.12 g, 28 m moles) in dimethyl sulfoxide (200 ml), for 4 hours. The resin is filtered and washed on the filter with ethanol, methylene chloride, 15% triethylamine in methylene chloride, dimethylformamide, methylene chloride and methanol (three times each). The peptide-resin is subjected to a ninhydrin test following the procedure of E. Kaiser, et al., Analytical Chemistry 34, 595 (1970). It should be negative at this state. The resin is determined to be substituted to the extent of 0.42 m moles of t-Boc-O-benzyl-L-serine per gram of resin.

The t-Boc-O-benzyl-L-serine resin (14.0 g, 5.6 m moles) is placed in a Beckman 990 peptide synthesizer reaction vessel and treated in the following manner:
1. methylene chloride (three times);
2. 5 minute prewash with 1:1 trifluoroacetic acid-methylene chloride (v/v containing 0.5% dithioerythritol;
3. 30 minute deprotection with the above described trifluoroacetic acid;
4. methylene chloride (six times);
5. 15% triethylamine in dimethylformamide (three times);
6. methylene chloride (six times). A contact time of 1.5 minutes is allowed for each wash unless otherwise indicated.

The resin is gently stirred with t-Boc-O-benzyl-L-threonine (11.2 g, 36 m moles in methylene chloride) and 40.0 ml of 1M, N,N' diisopropylcarbodiimide (DIC) in methylene chloride (DIC added in two equal portions over 30 minutes). After stirring for 4 hours the peptide-resin is washed successively with methylene chloride, dimethylformamide and methylene chloride (three times each). To test for completeness of reaction the peptide resin is subjected to a ninhydrin test. It should be negative (or nearly so) at this stage. Any unreacted sites are acylated with acetylimidazole (70 ml, 2.5% in methylene chloride) for 30 minutes and the resin washed with methylene chloride (six times).

The deprotection of the attached amino acid is carried out as described in steps (1) through (6) above.

The following amino acid residues are then introduced consecutively: t-Boc-L-phenylalanine (9.5 g, 36 m moles in methylene chloride, 40 m moles DIC), t-Boc-O-benzyl-L-threonine (11.2 g, 36 m moles in methylene chloride, 40 m moles DIC), t-Boc-N$^\epsilon$ -(2-chlorobenzyloxycarbonyl)-L-lysine (15.0 g. 36 m moles in 50% methylene chloride-dimethylformamide, 40 m moles DIC), t-Boc-L-trytophan (11.0 g, 36 m moles in dimethylformamide, 40 m moles DIC). Reaction time for each coupling is four hours unless noted otherwise. Following each coupling the peptide-resin is washed and acylated as described above. Removal of the α-amino protecting group at each step is performed as described for the deprotection of the t-Boc-L-serine-resin (steps 1–6). The washed hexapeptide-resin is dried, weighed (21.0 g) and the synthesis continued with 50% (10.5 g, 3 m moles) of the peptide-resin. The following amino acid residues are further introduced: t-Boc-L-phenylalanine (4.75 g, 18 m moles in methylene chloride, 20 m moles DIC), t-Boc-L-phenylalaine (4.75 g, 18 m moles in methylene chloride, 20 m moles DIC), t-Boc-L-asparagine-p-nitrophenylester (6.4 g, 18 m moles in 1% acetic acid-dimethylformamide, 24 hour coupling), t-Boc-N$^\epsilon$ -(2-chlorobenzyloxycarbonyl)-L-lysine (7.45 g, 18 mmoles in 50% methylene chloride-dimethylformamide, 20 m moles DIC). The decapeptide-resin is dried, weighed (12.2 g) and the synthesis continued with 5.0 g (1.1 m moles) of the peptide-resin. The next amino acid added is benzyloxycarbonyl-N$^\epsilon$ -(t-butyloxycarbonyl)-L-lysine-p-nitrophenylester (3.0 g, 6 m moles in 1% acetic acid-dimethylformamide, 24 hour coupling). After washing, the resin is dried in vacuo to yield 5.1 g of the above titled product.

EXAMPLE 2

Benzyloxycarbonyl-N$^\epsilon$ -(t-butyloxycarbonyl)-L-lysyl-(2-chlorobenzyloxycarbonyl)-L-lysyl-L-asparaginyl-L-phenylalanyl-L-phenylalanyl-L-tryptophyl-N$^\epsilon$ -(2-chlorobenzyloxycarbonyl)-L-lysyl-O:benzyl-L-threonyl-L-phenylalanyl-O-benzyl-L:threonyl-O-benzyl-L-seryl hydrazide The preparation (5.1 g,) obtained in Example 1 is suspended in dimethylformamide (50 ml) an stirred with hydrazine (2.0 ml, 62 m moles) for 48 hours (25° C.). The resin is then filtered and washed twice with dimethylformamide. The filtrate and washes are combined and concentrated under reduced pressure maintaining a temperature of <25° C. The resulting oil is triturated with water to yield a white precipitate. After filtration the precipitate is dried in vacuo to yield the above titled product (1.85 g). Amino acid analysis: Asp (1) 1.06; Thr (2) 1.90; Ser (1) 0.86; Phe (3) 3.00; Lys (3) 2.94; Trp not determined.

EXAMPLE 3

Benzyloxycarbonyl-N$^\epsilon$ -(t-butyloxycarbonyl)-L-lysyl-N$^\epsilon$ -(2-chlorobenzyloxycarbonyl)-L-lysyl-L-asparaginyl-L-phenylalanyl-L-phenyl-alanyl-L-tryptophyl-N$^\epsilon$ -(2-chlorobenzyloxycarbonyl)-L-lysyl-O-benzyl-L-threonyl-L-phenylalanyl-O-benzyl-L-threonyl-O-benzyl-L-seryl-$\alpha$-benzyl-$\beta$-tert-butyl-L-aspartate A solution of the protected undecapeptide hydrazide obtained in Example 2 (1.75 g, 0.76 m moles) in dimethylsulfoxide (5.0 ml)-dimethylformamide (14 ml) is cooled to −20° C, and 1.7 N hydrochloric acid in tetrahydrofuran (1.22 ml, 2.08 m moles) added. The bath is warmed to −15° C and t-butylnitrite (0.120 ml) added. The solution is stirred for 1 hour at −15° C and to it added H-Asp (O-t-butyl)-OBzl (0.276 g, 0.84 m moles) in dimethylformamide (4 ml). The pH of the reaction is adjusted to ≈ 8.0 with triethylamine and the reaction stirred at −15° C for 1 hour then at +5° C for 18 hours and 25° C for 3 hours. The mixture is concentrated under reduced pressure and the resulting oil triturated with water. The precipitate is filtered, washed with water and dried to yield 1.85 g of the above titled product.

EXAMPLE 4

N$^\epsilon$ -(benzyloxycarbonyl)-L-lysyl-N$^\epsilon$ -(2-chlorobenzyloxycarbonyl)-L-lysyl-L-asparaginyl-L-phenylalanyl-L-phenylalanyl-L-tryptophyl-N$^\epsilon$ -(2-chlorobenzyloxycarbonyl)-L-lysyl-O-benzyl-L:threonyl-L-phenylalanyl-O-benzyl-L:threonyl-O-benzyl-L-seryl-$\alpha$-benzyl-L-aspartate The above protected dodecapeptide (1.85 g) of Example 3 is treated with a 30% solution of trifluoroactic acid-methylene chloride (70 cc) containing dithioerythritol (0.5%) for 45 minutes at 25° C. The solution is concentrated to an oil and triturated with anhydrous ether. A white precipitate is filtered, washed with additional ether and dried to yield 1.80 g of the above titled product.

EXAMPLE 5

L-lysyl-L-lysyl-L-asparaginyl-L-phenylalanyl-L-phenylalanyl-L-trytophyl-L-lysyl-L-threonyl-L-phenylalanyl-L- acid cyclic ($12\beta \rightarrow 1\epsilon$)-peptide, triacetate The dodecapeptide, $\alpha$-Cbz-Lys-Lys(ClCbz)-Asn-Phe-Phe-Trp-Lys(ClCbz)-Thr(Bzl)-Phe-Thr(Bzl)-Ser(Bzl)-Asp(OH)OBzl (1.80 g, 0.72 m moles) of Example 4 is dissolved in 600 ml of dimethylformamidemethylene chloride (1:2). To the solution is added N-hydroxybenzotriazole (1.1 g, 15 eq.) and cooled in an ice bath. The pH of the reaction is adjusted to 7.5 with triethylamine. A solution of dicyclohexylcarbodiimide (1.18 g, 12 eq. in 10 ml dimethylformamide is added and the reaction stirred at 0° C for 3 hours then at 25° C for 5 days. The mixture is evaporated to an oil and triturated with water. After filtration the precipitate is washed thoroughly with water and dried. The dried solid (2.4 g) is treated in vacuo with anhydrous liquid hydrogen fluoride (70 ml) and anisole (10 ml) at 0° C for 45 minutes. The hydrogen fluoride and anisole are then removed under reduced pressure and the residue is suspended in ether. After filtering the residue is dissolved in 2 N acetic acid and lyophilized to leave the above titled crude product (1.25 g).

EXAMPLE 6

Purification and characterization of L-Lysyl-L-lysyl-L-asparaginyl-L-phenylalanyl-L-phenylalanyl-L-tryptophyl-L-lysyl-L-threonyl-L-phenylalanyl-L-threonyl-L-aspartic acid cyclic ($12\beta \rightarrow 1\epsilon$)-peptide, triacetate The above titled crude product obtained in Example 5 is purified as follows: 1.25 g of material is dissolved in a minimum amount of 2 N acetic acid and applied to a column (2.5 × 200 cm) of Sephadex G-25 (fine) in 2N acetic acid. The column effluent is monitored by the Folin-Lowry color reaction on every third fraction. Fractions 155–172 are combined and lyophilized to yield 250 mg of nearly pure product. The above material (250 mg) is applied to the same column as previously described and further purified. Fractions 161–171 are shown to be homogenous by thin layer chromatography systems 4:1:5 (n-butanol : acetic acid: water) and 7:7:6 (isoamyl alcohol : pyridine : water). Thin layer chromatograms are visualized with iodine and chlorine peptide reagent. R$_f$ 4:1:5 (cellulose) 0.60; (silica gel) 0.28; R$_f$ 7:7:6 (cellulose) 0.60).

After hydrolysis of the peptide in 4 N methanesulfonic acid for 18 hours (110° C) the following amino acid analysis was obtained: Asp, 1.86; Lys, 2.81; Phe, 3.00,; Trp. 0.73; Ser, 0.79; Thr, 1.92.

The effect on glucagon, growth hormone and insulin levels of the compound of Example 7 was determined by injecting rats weighing about 200–240 g first with nembutal intraperitoneally at a dose of 50 mg/kg then after 5 minutes injecting the rats subcutaneously with a solution of the compound of Example 7 in saline at a dose of 3.1 mg/kg per rat. Blood samples are taken 15 minutes after injection with the compound of Example 7. The glucagon, growth hormone and insulin levels were determined by radioimmunoassay. The results of the in vivo tests are reported in the table below.

| Compound | Dose µg/kg | GH ng/kg | Insulin µU/ml | Glucagon pg/ml | No. Animals |
|---|---|---|---|---|---|
| Compound of Example 7 | 3100 | 227 ± 32 | 182 ± 16 | 3.3 ± 0.8* | 10 |
| Somatostatin (SRIF) | 200 | 60 ± 6* | 107 ± 8* | 2.3 ± 0.8* | 10 |
| Control | | 296 ± 25 | 171 ± 4 | 10.5 ± 2 | 10 |

*p <0.01

The foregoing results indicate that the compound lowered glucagon levels without having any substantial effect on growth hormone and insulin activity. Thus, the compounds of formula I are highly specific in their activity in reducing glucagon levels without effecting growth hormone and insulin activity. Hence, these compounds have application in the treatment of diabetes mellitus because glucagon excess is known to be a principal factor in the overproduction of glucose in diabetes. See, for example, Unger et al., Lancet, pp 14–16 (Jan. 4, 1975).

The compound of formula I described herein may be administered to warm blooded mamals, including humans, either intravenously, subcutaneously, intramuscularly or orally to inhibit the release of glucagon where the host being treated requires therapeutic treatment for glucagon excess which is associated with diabetes mellitus. The contemplated dose range for oral administration in tablet or capsule form to large mammals is about 0.015 mg to about 7 mg/kg of body weight per day while the dose range for intravenous injection in an aqueous solution is about 0.14 μg to about 0.15 mg/kg of body weight per day. When administered subcutaneously or intramuscularly a dose range of about 1.5 μg to about 7 mg/kg of body weight per day is contemplated. Obviously, the required dosage will vary with the particular condition being treated, the severity of the condition and the duration of treatment.

If active ingredient is administered in tablet form the tablet may contain: a binder such as gum tragacanth, corn starch, gelatin, an excipient such as dicalcium phosphate; a disintegrating agent such as corn starch, alginic acid, etc.; a lubricant such as magnesium stearate; and a sweetening and/or flavoring agent such as sucrose, lactose, wintergreen, etc. Suitable liquid carriers for intravenous administration include isotonic saline, phosphate buffer solutions, etc.

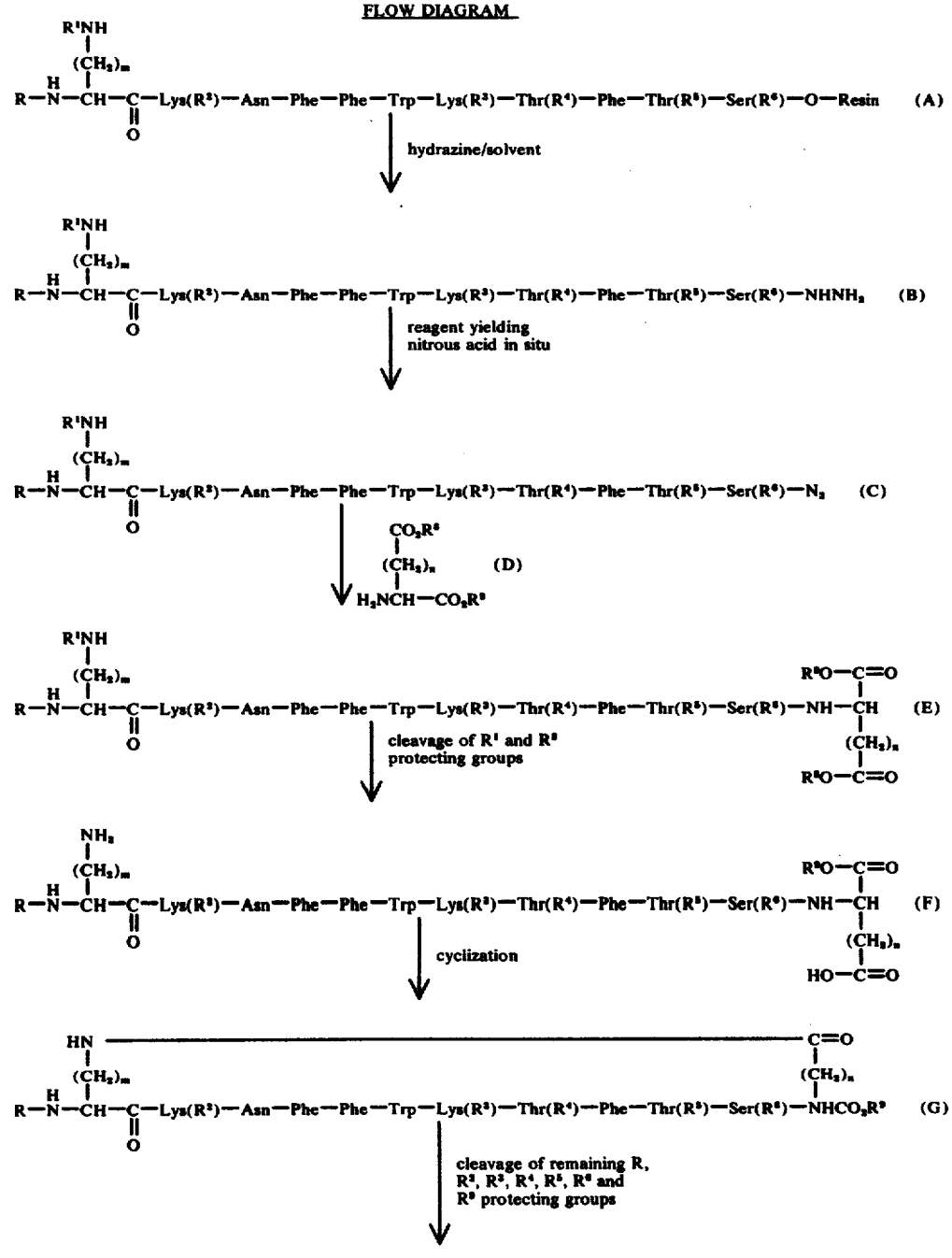

Formula I

What is claimed is:
1. A compound selected from the class consisting of

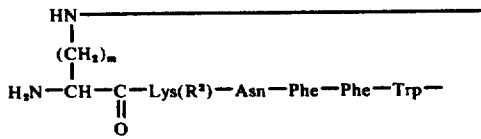

(I)

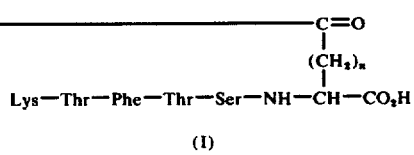

and

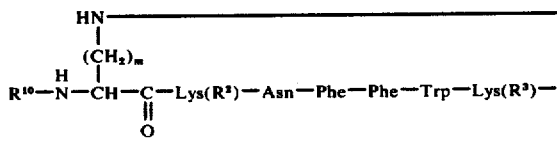

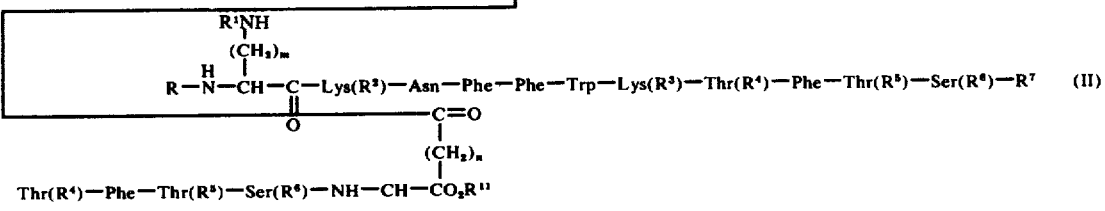

and the non-toxic acid salts thereof, wherein:

R² and R³ are selected from the class consisting of a protecting group for the side chain amino substituent selected from benzyloxycarbonyl, tosyl, t-amyloxycarbonyl, t-butyloxycarbonyl, diisopropylmethoxycarbonly and substituted benzyloxycarbonyl wherein said substituent is selected from halo and nitro;

R⁴, R⁵ and R⁶ are selected from the class consisting of hydrogen and a protecting group for the alcoholic hydroxyl group of threonine and serine selected from acetyl, benzoyl, tert-butyl, trityl, benzyl, 2,6 dichlorobenzyl and benzyloxycarbonyl;

R¹⁰ is selected from the class consisting of hydrogen and an α-amino protecting group;

R¹¹ is selected from the class consisting of hydrogen and an α-carboxyl protecting group selected from $C_1$–$C_6$ alkyl, benzyl, substituted benzyl, phenacyl, phthalimidomethyl, benzhydryl, trichloroethyl, 4-picolyl, β-methylthioethyl, 4-(methylthio)phenyl, said substituent on benzyl being selected from nitro, methyl and methoxy; and each of m and n is a whole number from 1 through 5; and all chiral amino acids identified in said formulas I and V being of the L-configuration.

2. A compound according to formula V of claim 1 wherein R² and R³ are 2-chlorobenzyloxycarbonyl, R⁴, R⁵ and R⁶ are benzyl, R¹⁰ is benzyloxycarbonyl, R¹¹ is benzyl, m is four and n is one.

3. A compound of the formula

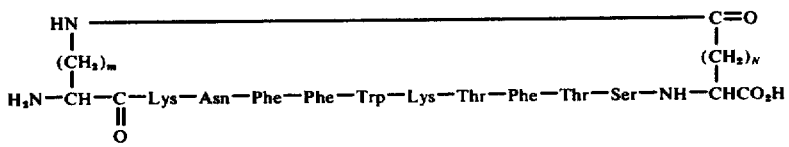

and its non-toxic salts, wherein each of m and n is a whole number from 1 through 5; and all chiral amino acids in said compound being of the L-configuration.

4. A compound according to claim 3 which is selected from L-lysyl-L-lysyl-L-asparaginyl-L-phenylalanyl-L-phenylalanyl-L-tryptophyl-L-lysyl-L-threonyl-L-phenylalanyl-L-threonyl-L-seryl-L-aspartic acid cyclic (12β → 1ε)peptide and a non-toxic salt thereof.

5. A compound of the formula wherein:

R is an α-amino protecting group that is not cleavable under conditions that will cleave the R¹ protecting group;

R¹ is an acid labile or photolytic labile protecting group that is cleavable under conditions that will not remove said R, R² R³ protecting groups;

R² and R³ is a protecting group for the side chain amino substituent of lysine selected from the class consisting of benzyloxycarbonyl, tosyl, t-amyloxycarbonyl, t-butyloxycarbonyl, diisopropylmethoxycarbonyl and substituted benzyloxycarbonyl, said substituent selected from halo and nitro and said R² and R³ groups being stable to cleavage under conditions that result in cleavage of said R¹ group;

R⁴, R⁵ and R⁶ are selected from the class consisting of hydrogen and a protecting group for the alcoholic hydroxyl group of threonine and serine selected from acetyl, benzoyl, tert-butyl, trityl, benzyl, 2,6 dichlorobenzyl and benzyloxycarbonyl; and R⁷ is selected from the class consisting of OH, $NHNH_2$, $N_3$, $OCH_3$ and

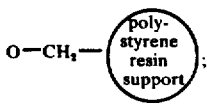

m is a whole number from 1 through 5; and all chiral amino acids in said compound being of the L-configuration.

6. A compound according to claim 5 wherein R is benzyloxycarbonyl, $R^1$ is t-butyloxycarbonyl, $R^2$ and $R^3$ are 2-chlorobenzyloxycarbonyl and $R^4$, $R^5$ and $R^6$ are benzyl.

7. A compound according to claim 6 wherein $R^7$ is $NHNH_2$.

8. A compound according to claim 6 wherein $R^7$ is

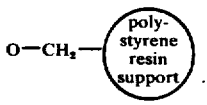

9. A compound selected from those of the formula hydroxyl group of threonine and serine selected from acetyl, benzoyl, tert-butyl, trityl, benzyl, 2,6-dichlorobenzyl and benzyloxycarbonyl;

$R^8$ is a side chain carboxyl protecting group which is removable under conditions that will not remove the $R^9$ carboxyl protecting group;

$R^9$ is an α-carboxyl protecting group which is stable under reaction conditions which cleave said $R^1$ and $R^8$ protecting groups, said α-carboxyl protecting group being selected from the class consisting of $C_1$–$C_6$ alkyl, benzyl, phenacyl, phthalimidomethyl, benzhydryl, trichloroethyl, 4-picolyl, β-methylthioethyl, 4-(methylthio)phenyl and substituted benzyl, said substituent being selected from the class consisting of nitro, methoxy and methyl;

$R^{13}$ is selected from the class consisting of hydrogen and $R^1$;

$R^{14}$ is selected from the class consisting of hydrogen and $R^8$; at least of $R^{13}$ and $R^{14}$ being hydrogen; each of m and n is a whole number from 1 through 5; all chiral amino acids in said compounds being of the L-configuration.

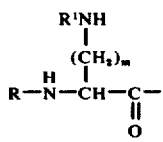 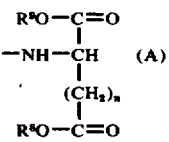

and

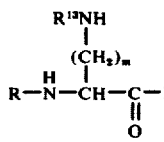 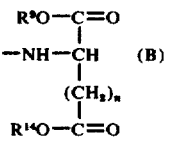

wherein:

R is an α-amino protecting group that is not cleavable under conditions that cleave the $R^1$ protecting group;

$R^1$ is an acid labile or photolytic labile protecting group that is cleavable under conditions that will not remove said R, $R^2$ and $R^3$ protecting groups;

$R^2$ and $R^3$ are protecting groups for the side chain amino substituent of lysine selected from the class consisting of benzyloxycarbonyl, tosyl, t-amyloxycarbonyl, t-butyloxycarbonyl, diisopropylmethoxycarbonyl and substituted benzyloxycarbonyl, said substituent being selected from halo and nitro, said $R^2$ and $R^3$ groups being stable to cleavage under conditions that result in cleavage of said $R^1$ group;

$R^4$, $R^5$ and $R^6$ are selected from the class consisting of hydrogen and a protecting group for the alcoholic 10. A compound according to claim 9 represented by formula A wherein R is benzyloxycarbonyl, $R^2$ and $R^3$ are 2-chlorobenzyloxycarbonyl, $R^4$, $R^5$ and $R^6$ are benzyl, $R^8$ is t-butyl, $R^9$ is benzyl and $R^{13}$ is t-butyloxycarbonyl.

11. A compound according to claim 9 represented by formula B wherein R is benzyloxycarbonyl, $R^2$ and $R^3$ are 2-chlorobenzyloxycarbonyl, $R^4$, $R^5$ and $R^6$ are benzyl, $R^8$ is hydrogen, $R^9$ is benzyl and $R^{13}$ and $R^{14}$ are hydrogen.

12. A compound of the formula

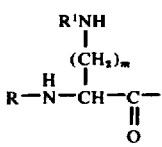 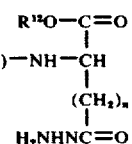

wherein:

R is an α-amino protecting group that is not cleavable under conditions that cleave the $R^1$ protecting group;

$R^1$ is an acid labile or photolytic labile protecting group that is cleavable under conditions that will not remove said R, $R^2$ and $R^3$ protecting groups;

$R^2$ and $R^3$ are protecting groups for the side chain amino substituent of lysine selected from the class consisting of benzyloxycarbonyl, tosyl, t-amyloxycarbonyl, t-butyloxycarbonyl, diisopropylmethoxycarbonyl and substituted benzyloxycarbonyl, said substituent being selected from halo and nitro, said $R^2$ and $R^3$ groups being stable to cleavage under conditions that result in cleavage of said $R^1$ group;

$R^4$, $R^5$ and $R^6$ are selected from the class consisting of hydrogen and a protecting group for the alcoholic hydroxyl group of threonine and serine selected from acetyl, benzoyl, tert-butyl, trityl, benzyl, 2,6-dichlorobenzyl and benzyloxycarbonyl;

$R^{12}$ is selected from the class consisting of hydrogen and an α-carboxyl protecting group selected from the class consisting of $C_1$–$C_6$ alkyl, benzyl, phenacyl, phthalimidomethyl, benzhydryl, trichloroethyl, 4-picolyl, β-methylthioethyl, 4-(methylthio)phenyl and substituted benzyl, said sutstituent being selected from the class consisting of nitro, methoxy and methyl; each of m and n is a whole number from 1 through 5; all chiral amino acids in said compounds being of the L-configuration.

13. A method of treating diabetes mellitus in a mammal having a diabetic condition which comprises administering to said mammal an effective amount of inhibiting the secretion of glucagon of a compound of the formula L-lysyl-L-lysyl-L-asparaginyl-L-phenylalanyl-L-phenylalanyl-L-tryptophyl-L-lysyl-L-threonyl-L-phenylalanyl-L-threonyl-L-seryl-L-aspartic acid cyclic (12β → 1ε) peptide or a non-toxic salt thereof.

* * * * *